(12) United States Patent
Choi et al.

(10) Patent No.: US 9,681,840 B2
(45) Date of Patent: Jun. 20, 2017

(54) WEARABLE MOBILE DEVICE AND METHOD OF MEASURING BIOLOGICAL SIGNAL WITH THE SAME

(71) Applicant: Samsung Electronics Co., Ltd., Suwon-si (KR)

(72) Inventors: Chang Mok Choi, Seoul (KR); Sang Joon Kim, Hwaseong-si (KR); Sang Il Park, Seoul (KR); Se O Lee, Yongin-si (KR); Young Joong Jun, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/221,178

(22) Filed: Jul. 27, 2016

(65) Prior Publication Data
US 2016/0331324 A1 Nov. 17, 2016

Related U.S. Application Data

(63) Continuation of application No. 14/304,366, filed on Jun. 13, 2014, now Pat. No. 9,427,158.

(30) Foreign Application Priority Data

Nov. 26, 2013 (KR) ........................ 10-2013-0144550

(51) Int. Cl.
*A61B 5/00* (2006.01)
*A61B 5/0205* (2006.01)
(Continued)

(52) U.S. Cl.
CPC .......... *A61B 5/6843* (2013.01); *A61B 5/0015* (2013.01); *A61B 5/0082* (2013.01); *A61B 5/026* (2013.01); *A61B 5/02055* (2013.01); *A61B 5/0402* (2013.01); *A61B 5/0488* (2013.01); *A61B 5/0531* (2013.01); *A61B 5/117* (2013.01);
(Continued)

(58) Field of Classification Search
CPC ....... A61B 5/0015; A61B 5/6843; A61B 5/02; A61B 5/6813; A61B 5/6824; A61B 5/7271
See application file for complete search history.

(56) References Cited

U.S. PATENT DOCUMENTS

| 6,244,873 | B1 | 6/2001 | Hill et al. | |
|---|---|---|---|---|
| 8,461,998 | B2 | 6/2013 | Ruhs et al. | |
| 2009/0118651 | A1* | 5/2009 | Rousso ................. | A61H 11/00 601/134 |
| 2010/0152620 | A1 | 6/2010 | Ramsay et al. | |
| 2011/0263950 | A1 | 10/2011 | Larson et al. | |

(Continued)

FOREIGN PATENT DOCUMENTS

| JP | 2004-298606 A | 10/2004 |
|---|---|---|
| JP | 4325344 B2 | 9/2009 |

(Continued)

OTHER PUBLICATIONS

Extended European Search Report issued Sep. 10, 2014 in counterpart European Application No. 14179451.1 (6 pages).

*Primary Examiner* — Hongmin Fan
(74) *Attorney, Agent, or Firm* — NSIP Law (57) ABSTRACT

A wearable mobile device and a method of detecting a biosignal with a wearable mobile device are provided. A method of detecting a biosignal with a wearable mobile device involves determining whether a wearable mobile device is closely attached to a user; and providing a biosignal-based service in response to the wearable mobile device being determined to be closely attached to the user.

13 Claims, 6 Drawing Sheets

(51) Int. Cl.
*A61B 5/053* (2006.01)
*A61B 5/117* (2016.01)
*G08B 21/18* (2006.01)
*A61B 5/026* (2006.01)
*A61B 5/0402* (2006.01)
*A61B 5/0488* (2006.01)
*G08B 21/04* (2006.01)
*A61B 5/024* (2006.01)

(52) U.S. Cl.
CPC ........ *A61B 5/6824* (2013.01); *G08B 21/0453* (2013.01); *G08B 21/18* (2013.01); *A61B 5/02416* (2013.01); *A61B 5/02438* (2013.01); *A61B 5/7271* (2013.01); *A61B 2562/0257* (2013.01)

(56) References Cited

U.S. PATENT DOCUMENTS

| | | |
|---|---|---|
| 2012/0295589 A1 | 11/2012 | Alexander et al. |
| 2013/0158368 A1 | 6/2013 | Pacione et al. |
| 2015/0031964 A1* | 1/2015 | Bly ................. A61B 5/165 600/301 |

FOREIGN PATENT DOCUMENTS

| | | |
|---|---|---|
| KR | 10-2006-0044057 A | 5/2006 |
| KR | 10-2009-0019369 A | 2/2009 |
| KR | 10-2010-0072993 A | 7/2010 |
| KR | 10-1207386 B1 | 12/2012 |
| KR | 10-1329847 B1 | 11/2013 |
| WO | WO 2012/115943 A1 | 8/2012 |

* cited by examiner

WEARABLE MOBILE DEVICE AND METHOD OF MEASURING BIOLOGICAL SIGNAL WITH THE SAME

CROSS-REFERENCE TO RELATED APPLICATION(S)

This application is a continuation of U.S. patent application Ser. No. 14/304,366, filed on Jun. 13, 2014, which claims the benefit under 35 USC 119(a) of Korean Patent Application No. 10-2013-0144550 filed on Nov. 26, 2013, in the Korean Intellectual Property Office, the entire disclosure of which is incorporated herein by reference for all purposes.

BACKGROUND

1. Field

The following description relates to a wearable mobile device and a method of detecting a biosignal with a wearable mobile device.

2. Description of Related Art

The widespread use of smart mobile terminals is resulting in the development of new forms of wearable mobile devices as well as diversification of such devices.

Some wearable mobile devices are equipped not only with a function of displaying information about a mobile terminal, but also with a function of detecting a biological signal from a user to monitor the health conditions of the user. Wearable mobile devices that measure biosignals are implemented in various configurations. For example, one type of such devices is a watch-type device that may monitor a heart rate of the user wearing the device using a photoplethysmography (PPG) sensor.

To detect a biological signal from the body of the user, a sensor in a watch-type device needs to be attached close to the skin of the user. However, to achieve the close contact between the sensor and the skin, the device may be positioned unnecessarily and excessively tight around the skin. Accordingly, a user wearing such a wearable mobile device may feel that his or her wrist or body part wearing the device is constricted by the device.

Furthermore, the constriction experienced by the user may intensify due to the fact that the wearable mobile device is closely attached to the skin at all times, even when the device is not detecting the biological signals from the user. Accordingly, it is desirable to produce a wearable mobile device that accurately detects biological signals while providing comfort to the user.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a method of measuring a biosignal, the method comprising determining whether a wearable mobile device is closely attached to a user, and providing a biosignal-based service in response to the wearable mobile device being determined to be closely attached to the user.

The providing may involve executing a program for sensing a biosignal from the user or a program that uses the sensed biosignal, and providing a result from the executed program as the biosignal-based service.

The determining may involve measuring a range or a position at which the wearable mobile device contacts the user, and determining that the wearable mobile device is closely attached to the user in response to the measured range satisfying a predetermined standard value or in response to the measured position corresponding to a predetermined skin area of the user.

In another general aspect, there is provided a method of using a wearable mobile device, the method involving attaching a bracelet comprising a sensor to an user, determining whether the sensor is closely attached to the user based on a movement of the bracelet during attachment to the user, and sensing the biosignal from the user by activating the sensor in response to a determination that the sensor is closely attached to the user.

The determining may involve placing an analog front end of the sensor in contact with a body of the user, and determining that the bracelet is closely attached to the user in response to the analog front end being not in a leadoff state.

The determining may involve sending a microcurrent to a body of the user through the analog front end of the sensor, and determining that the bracelet is closely attached to the user in response to an impedance measured based on a return of the sent microcurrent satisfying a predetermined value.

In the general aspect of the method, the bracelet may further include an additional sensor for determining whether the bracelet is closely attached to the user, and the determining may involve determining that the bracelet is closely attached to the user in response to the additional sensor entering an operating state based on a body position at which the bracelet is attached to the user.

The sensing may involve identifying an activated sensor based on a body position at which the bracelet is closely attached to the user, and sensing the biosignal by the identified sensor.

The general aspect of the method may further include, in response to determining that the bracelet is closely attached to the user, executing a program associated with the biosignal or adjusting a system environment to be a predetermined value.

The general aspect of the method may further include outputting a result of the determining of whether the bracelet is closely attached to the user.

In another general aspect, a wearable mobile device includes a bracelet configured to be attached to a user by surrounding a body of the user, a determiner configured to determine whether the bracelet is closely attached to the user based on a movement of the bracelet during attachment to the user, and a sensor unit including sensors configured to sense a biosignal from the user subsequent to activation in response to the determiner determining that the bracelet is closely attached to the user.

An analog front end in the sensors may be in contact with the body of the user, and the determiner may be configured to determine that the bracelet is closely attached to the user in response to the analog front end being not in a leadoff state.

The analog front end in the sensors may be configured to send a microcurrent to the body of the user, and the determiner may be configured to determine that the bracelet is closely attached to the user in response to an impedance measured based on a return of the sent microcurrent satisfying a predetermined value.

The bracelet may further include an additional sensor for determining whether the bracelet is closely attached to the user, and the determiner may be configured to determine that the bracelet is closely attached to the user based on a body position at which the bracelet is attached to the user in response to the additional sensor entering an operating state.

The sensor unit may be configured to identify an activated sensor based on a body position at which the bracelet is closely attached to the user and sense the biosignal by the identified sensor.

The general aspect of the device may further include a controller configured to, in response to the bracelet being determined to be closely attached to the user, execute a program associated with the biosignal or adjust a system environment to be a predetermined value.

The general aspect of the device may further include an output unit configured to output a result of the determining of whether the bracelet is closely attached to the user.

In a general aspect, a wearable mobile device includes a band portion configured to detachably attach the wearable mobile device to a user, the band portion comprising a sensing surface configured to contact a skin of the user, a processor configured to determine a contact state of the sensing surface and the skin as at least one of: a close contact state and a loose state, and a sensor unit comprising a biosignal sensor configured to sense a biosignal via the skin in response to the processor determining that the sensing surface is in a close contact state.

The sensor unit may be configured to inactivate the biosignal sensor in response to the processor determining that the sensing surface is in a loose state.

The general aspect of the wearable mobile device may further include a contact detecting sensor disposed on the band portion, and the contact detecting sensor may be configured to detect a signal used by the processor to determine the contact state of the sensing surface with the skin of the user.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

To accurately detect a signal from the body of the user, a sensor of a wearable mobile device needs to be positioned close to the skin. However, having a mobile device tightly attached to a body part may cause uncomfortable feeling of constriction. Further, having the wearable mobile device attached closely to the skin even when the biological signals are not being detected may make it undesirable for the user to wear the mobile device at all times.

An improved wearable mobile device that allows a close attachment to the skin while biosignals are detected, and allows a loose attachment while biosignals are not detected may improve the user experience. Further, the displayed content of the wearable mobile device may be further controlled based on whether the biological signals are being detected or whether the mobile device is in a close contact to detect the biological signals, so that unnecessary information does not take up the limited display space.

A sensor unit described herein refers to a sensor or a set of sensors that may be attached to an object such as a body part of a user or a target, and detects a signal generated from the object. The detected signal may include an electrocardiogram (ECG), a photoplethysmogram (PPG), an impedance, an electromyogram (EMG), or other biological signal associated with the user. The sensor or the set of sensors included in the sensor unit may refer to a PPG sensor, an EMG sensor, and the like that may be used to monitor the contraction and relaxation of muscles or may sense various types of biosignals. In addition to such sensors, the sensor unit may include an additional sensor such as, for example, a temperature sensor, a force sensor, and an illuminance sensor, that may be used to determine whether a wearable mobile device is closely attached to the user. When the wearable mobile device is closely attached to the user, the wearable mobile device may be referred to as being in a close contact state. When the wearable mobile device is determined to be not closely attached even though the mobile device is attached to the user, the wearable mobile device may be determined to be in a loose state.

A bracelet may include the sensor unit that includes the sensor or the set of sensors. The bracelet may be detachably attached to a human body. The bracelet may be implemented in a variety of different format. For example, the bracelet may have the format of a ring-shaped structure that may be attached to a user by allowing a hand of the user to pass through the ring-shaped structure to position the ring-shaped structure around the wrist of the user. In another example, the bracelet may have a semi-ring shape to be attached by allowing the wrist to pass through an open portion of a ring. In another example, the bracelet may have a hinge shape to allow the wrist to pass through a ring by opening a portion of the ring and closing the opened portion of the ring after the wrist is positioned in the ring.

For example, when a ring-shaped bracelet is attached to an arm, which is the target object, the sensor unit disposed in the bracelet may be used to detect a biosignal generated from an arm muscle. In detecting a biosignal, the sensor unit may detect the biosignal generated from the arm muscle when the bracelet moves towards a forearm having a relatively greater circumference and thereby, being closely attached to the arm.

Conversely, the sensor unit may suspend the detection of a biosignal in response to the bracelet moving towards the wrist having a relatively small circumference and thereby, being loosely attached to the arm. Thus, the sensor unit may selectively detect the biosignal based on whether the bracelet is closely attached to the user or loosely attached to the user.

A wearable mobile device described herein may provide a biosignal-based service by activating the sensor unit and allowing the sensor unit to sense a biosignal when the bracelet is determined to be closely attached to the user.

The wearable mobile device may provide the biosignal-based service in response to a simple action of the user closely attaching the bracelet to the body part without requiring an additional operation from the user. For example, the user may use his or her hand to bring the sensor region of the bracelet in firm contact with the skin underneath. Based on the pressure, the wearable mobile device may activate the sensor unit, without pushing any button or manipulating any object in the digital display screen. Thus, convenience may be further improved.

Figure 1A:
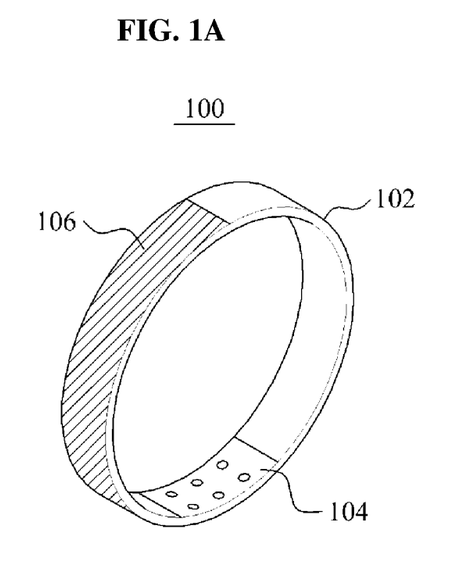
FIG. 1A is a diagram illustrating an example of a wearable mobile device.
Figure 1B:
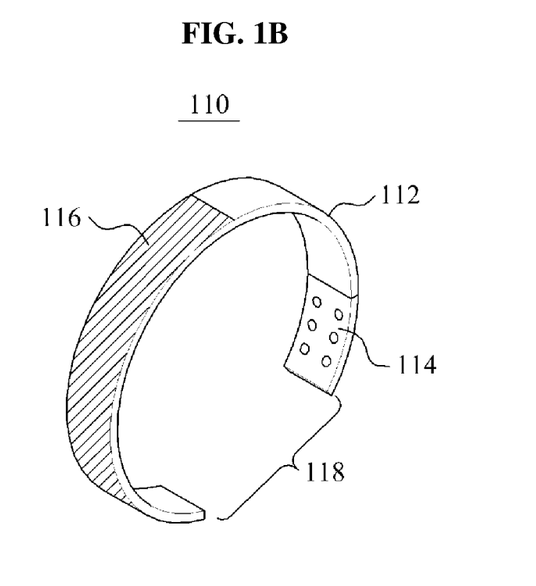
FIG. 1B is a diagram illustrating another example of a wearable mobile device.

FIGS. 1A and 1B are diagrams illustrating examples of wearable mobile devices 100 and 110.

Referring to FIGS. 1A and 1B, a wearable mobile device 100 of FIG. 1A and a wearable mobile device 110 of FIG. 1B are implemented in a form of a bracelet or a wrist watch that may be worn around a body part of a user to be attached to the user.

The wearable mobile devices 100 and 110 may include band portions 102 and 112 configured to attach the wearable mobile devices 100 and 110 to a body part such as a wrist, sensor units 104 and 114 configured to detect a biosignal of the user via from the body part, and display units 106 and 116 configured to provide visual user interface regarding a biosignal-based service to the user. The display units 106 and 116 may be configured to display time or provide other services to the user in addition to providing a biosignal-based service. Referring to FIG. 1B, the wearable mobile device 110 may include a gap 118 at which a portion of a ring that forms the bracelet is open. The gap 118 may allows a user to insert his or her wrist into the ring.

The band portions 102 and 112 may attach the wearable mobile devices 100 and 110 to the user by surrounding the body part of the user. The band portions 102 and 112 of the bracelet may include the sensor units 104 and 114 and the display units 106 and 116, respectively, and obtain a biosignal and provide necessary information while attached to the user.

In an example, the band portions 102 and 112 may be composed of a hard material. Thus, exteriors of the bracelets may not be easily deformed by an external force. When mounted on a wrist of the user, for example, the space between the wrist and the band portions 102 and 112 may form a gap and allow the bracelet to loosely attach to the wrist. In an example, the band portions 102 and 112 may not permanently tighten the body of the user due to an elastic property of the band portions 102 and 112. Accordingly, a period of time during which the band portions 102 and 112 are closely attached to the user and a period of time during which the band portions 102 and 112 are loosely attached to the user may be classified in accordance with a service desired by the user.

In another example, the band portions 102 and 112 may be formed of a flexible material having elasticity, and selectively detect a biosignal from the user based on a transformation of the band portions 102 and 112 induced by the elasticity. The band portions 102 and 112 may be classified, based on a range or a position at which the band portions 102 and 112 are attached to the user, the period of time during which the band portions 102 and 112 are closely attached to the user to allow the sensors 104 and 114 to detect a biosignal and the period of time during which the band portions 102 and 112 are loosely attached to the user to disallow detection of a biosignal by the sensors 104 and 114.

For example, when the band portions 102 and 112 are mounted on a wrist of a user, the wearable mobile devices 100 and 110 may determine that the band portions 102 and 112 are not closely attached to the user. Conversely, when the band portions 102 and 112 are attached to the user is a forearm having a relatively greater circumference than the wrist, the wearable mobile devices 100 and 110 may determine that band portions 102 and 112 are closely attached to the user. Also, when the range in which the band portions 102 and 112 are attached to the user exceeds a predetermined standard value, despite the user to which the band portions 102 and 112 are attached being the wrist, the wearable mobile devices 100 and 110 may determine that the band portions 102 and 112 are closely attached to the user.

Referring to FIG. 1A, the band portion 102 may be implemented in a shape of a ring to be attached to the use by allowing the hand of the user to pass through the ring. Referring to FIG. 1B, the band portion 112 may be implemented in a shape of a semi-ring including the gap 118. The band portion 112 may further include a hinge (now shown) that may allow the bracelet to be attached to the wrist by closing the opened portion of the ring after the wrist passes through the gap 118.

The sensor units 104 and 114 may include at least one sensor that may detect various types of biosignals from the user. The sensor units 104 and 114 may obtain the biosignals from the user through the sensor during the bracelets being closely attached to the user. The biosignals detected by the sensor units 104 and 114 may include an ECG, a PPG, an impedance, an EMG, and the like.

The display units 106 and 116 may provide a visual biosignal-based service generated in associated with the detected biosignals.

For example, when the biosignals detected by the sensor units 104 and 114 are associated with heart rates, information on the heart rates at which a most amount of weight may be lost by aerobic exercise may be fed back to the displays 106 and 116 and displayed as the biosignal-based service.

For another example, when the biosignals detected by the sensor units 104 and 114 are associated with the EMG, the displays 106 and 116 may execute, as the biosignal-based service, a program for controlling peripheral devices by a movement, for example, a hand gesture, of the user.

For still another example, when the biosignals detected by the sensor units 104 and 114 are associated with the impedance, information on a calculated amount of body fat may be fed back to the display units 106 and 116 and displayed as the biosignal-based service.

The detecting of the biosignals and the providing of the biosignal-based service may be performed when the sensor units 104 and 114 are closely attached to the user.

However, when the sensor units 104 and 114 are not closely attached to the user, the detecting of the biosignals is suspended, and the display units 106 and 116 may provide a service to communicate with a connected terminal, for example, displaying information on a smartphone, or a service that is not directly related to the biosignals.

The wearable mobile devices 100 and 110 may further include an accelerometer that may monitor a quantity of utilization of the wearable mobile devices 100 and 110. The display units 106 and 116 may visually provide the monitored quantity of utilization when the sensor units 104 and 114 and the band portions 102 and 112 of the bracelet are not closely attached to the user.

The wearable mobile devices 100 and 110 may detect a biosignal by allowing the sensor units 104 and 114 to be closely attached to the user exclusively when the detection of the biosignal is necessary. Also, the wearable mobile devices 100 and 110 may selectively measure heart rates during an exercise period, measure an EMG to control a home electronic appliance by a gesture, or measure an impedance to authenticate the user.

Thus, the wearable mobile devices 100 and 110 may be closely worn on skin of the user when detection of a biosignal is required, and be loosely worn when detection of the biosignal is not required.

The wearable mobile devices 100 and 110 may determine whether the band portions 102 and 112 are closely attached to the user. In one example, the wearable mobile devices 100 and 110 may determine whether the portion of the band including the sensor units 104 and 114 are contacting the skin or pressed against the skin of the user. The wearable mobile devices 100 and 110 may determine whether a biosignal is to be measured based on a degree of contact between the sensor units 104 and 114 and the skin of the user.

In an example, to determine whether the band portions 102 and 112 are closely attached to the user, the wearable mobile devices 100 and 110 may measure a numerical range in which the wearable mobile devices 100 and 110 are in contact with the user, and determine that the sensor units 104 and 114 are closely attached to the user when the measured numerical range satisfies a predetermined standard value. The wearable mobile devices 100 and 110 may recognize whether the bracelets are closely attached to the user based on the numerical range in which the wearable mobile devices 100 and 110 are in contact with the user. For example, when the range in which the wearable mobile devices 100 and 110 are in contact with the user is a greater than or equal to 95% of an internal area of the ring form, the wearable mobile devices 100 and 110 may determine that the band portions 102 and 112 are closely attached to the user.

In another example, the wearable mobile devices 100 and 110 may measure a position at which the wearable mobile devices 100 and 110 are in contact with the user, and may determine that the band portions 102 and 112 of the bracelets are closely attached to the user in response to the measured position corresponds to a predetermined skin area of the user. The wearable mobile devices 100 and 110 may recognize a degree of contact with the user based on the position at which the wearable mobile devices 100 and 110 are in contact with the user. For example, when the wearable mobile devices 100 and 110 are attached to a wrist of the user and move towards a forearm having a relatively greater circumference than the wrist, and are positioned on the forearm, the wearable mobile devices 100 and 110 may determine that the band portions 102 and 112 are closely attached to the user. The position of the wearable mobile devices 100 and 110 on the user may be measured by an additional sensor that may be included in the band portions 102 and 112. A more detailed description will be provided hereinafter.

In response to a determination that the wearable mobile devices are closely attached to the user, the wearable mobile devices 100 and 110 may provide the biosignal-based service. The wearable mobile devices 100 and 110 may activate the sensor units 104 and 114 after the band portions 102 and 112 are determined to be closely attached to the user, and may provide the biosignal-based service using a biosignal obtained through the sensor units 104 and 114 being activated.

For example, the band portions 102 and 112 are closely attached to the user, the wearable mobile devices 100 and 110 may activate a PPG sensor to measure heart rates, and may provide an exercise management service associated with the heart rates as the biosignal-based service.

For another example, in response to the band portions 102 and 112 being closely attached to the user, the wearable mobile devices 100 and 110 may activate an EMG sensor to measure a biosignal associated with a movement of the user, and may provide a gesture-based control service for a home appliance as the biosignal-based service.

For still another example, when the band portions 102 and 112 are closely attached to the user, the wearable mobile devices 100 and 110 may activate an EMG sensor to measure an impedance, and may provide an individual authentication service associated with the impedance as the biosignal-based service.

To provide the biosignal-based service, the wearable mobile devices 100 and 110 may execute a program for detecting a biosignal from the user or a program using the detected biosignal, and may provide a result output by the executed program as the biosignal-based service.

Based on the close contact with the user, the wearable mobile devices 100 and 110 may automatically execute a predetermined program associated with the biosignal, and may provide a result of the measurement of the biosignal and information about the result based on the execution of the program.

In an example, the band portions 102 and 112 of the wearable mobile devices 100 and 110 may be composed of a hard material that may not be easily deformed by an external force and thus, the user may not need to intentionally adjust a length of the band portions 102 and 112. The wearable mobile devices 100 and 110 may refer to a general fact that a forearm may be thicker than a wrist and the wrist may be thinner than the forearm, and may allow the user to raise the wearable mobile devices 100 and 110 towards the forearm when in need of detecting a biosignal and to lower the wearable mobile devices 100 and 110 towards the wrist when not in need of detecting the biosignal. Accordingly, the user may conveniently change wearability of the wearable mobile devices 100 and 110.

Also, the wearable mobile devices 100 and 110 may independently determine whether the wearable mobile devices 100 and 110 are closely attached to an arm of the user and determine whether to provide the biosignal-based service based on the determination. Accordingly, the wearable mobile devices 100 and 110 may increase a level of convenience by allowing the user to use the service without requiring an additional operation from the user.

Figure 2:
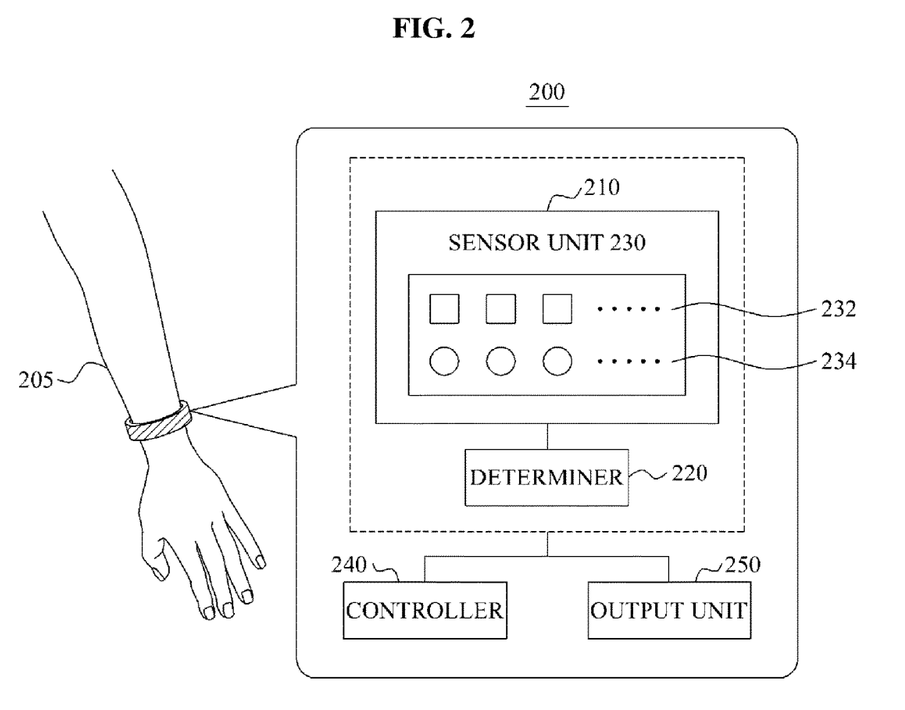
FIG. 2 is a diagram illustrating a configuration of an example of a wearable mobile device.

FIG. 2 is a diagram illustrating an example of a configuration of a wearable mobile device 200.

Referring to FIG. 2, the wearable mobile device 200 includes a bracelet having a band portion 210, a determiner 220, and a sensor unit 230. Also, the wearable mobile device 200 further includes a controller 240 and an output unit 250. The determiner 220 may operate on a processor.

The band portion 210 may detachably attach the wearable mobile device 200 to an user 205 by surrounding the user 205. The wearable mobile device 200 may be mounted on the user 205 through the band portion 210 of the bracelet.

The band portion 210 may include the sensor unit 230 in which at least one sensor 232 may be disposed at regular intervals. The sensor 232 of the wearable mobile device 200 may be positioned such that, when the band portion 210 is attached to the user, the sensor 232 affixed in the sensor unit 230 exposes a sensing surface to contact the user 205. The sensing surface refers a surface that may be in contact with the user 205 and may directly sense a biosignal generated from the user 205. The sensor 232 may be disposed on the sensing surface. For example, the sensing surface may sense a broad range of biosignals such as a bioelectrical/biomagnetic signal, bioimpedance signal, and a biodynamical signal of the user 205.

The band portion 210 of the bracelet may be initially attached to a wrist of a user and may be subsequently attached to a forearm of the user so that the sensing surface on which the sensing unit 230 is disposed is closely attached to the skin of the forearm by moving towards the forearm to acquire a biosignal-based service based on an intention of the user. In response to a determination that the sensor unit 230 is closely attached to the user 205, the sensor unit 230 may collect biosignals from all ranges of muscles of the forearm, which may be the user 205, through the sensor 232.

The determiner 220 may determine whether the band portion 210 is closely attached to the user 205 based on a movement of the bracelet during attachment to the user. The determiner 220 may verify a degree of contact between the bracelet and the user 205 and may arrange an environment in which the biosignal-based service is selectively provided based on the verified degree of contact.

The determiner 220 may measure a range or a position at which the bracelet is attached to the user 205, and may determine that the bracelet is closely attached to the user 205 in response to the measured range satisfying a predetermined standard value or the measured position corresponding to a predetermined skin area of the user 205.

Also, the determiner 220 may determine whether the bracelet is closely attached to the user 205 through an analog front end of the sensor 232 that may be disposed in contact with the user 205. The analog front end may indicate a front electrode and a rear electrode of the sensor 232 that may be responsible for detection.

In response to the analog front end not being in a leadoff state, the determiner 220 may determine that the wearable mobile device 200 is closely attached to the user 205. The determiner 220 may determine whether the wearable mobile device 200 is closely attached to the user 205 by verifying the leadoff state in which the wearable mobile device 200 has a modest degree of separation from the user 205 and the analog front end is not able to optimally collect signals from the user 205. For example, at a point in time when the analog front end is placed into contact with the user 205, the analog front end may send a signal to the user 205. When the analog front end receives a return of the signal from the user 205, the determiner 220 may determine that the analog front end is in an actual contact with the user 205 and not in the leadoff state; thus, the determiner 220 may determine that the wearable mobile device 200 is closely attached to the user 205.

The determiner 220 may determine whether the wearable mobile device 200 is closely attached to the user 205 based on a microcurrent sent from the analog front end to the user 205. When an impedance measured based on a return of the sent microcurrent satisfies a predetermined value, the determiner 220 may determine that the wearable mobile device 200 is closely attached to the user 205. For example, when the analog front end sends the microcurrent to the user 205 at a point in time when the analog front end is placed into contact with the user 205, the determiner 220 may calculate the impedance based on the microcurrent returning from the user 205, and may determine that the wearable mobile device 200 is closely attached to the user 205 by identifying that the calculated impedance exceeds the predetermined value, for example, 100 milliohms (m$\Omega$).

The determiner 220 may determine whether the wearable mobile device 200 is closely attached to the user 205 using an additional sensor 234 that may be additionally included in the band portion 210. The additional sensor 234 may include a temperature sensor used to sense a temperature emitted from the user 205, a force sensor used to sense a pressure applied by the user 205, an illuminance sensor used to detect brightness in the user 205 based on a degree of contact, and the like. The additional sensor 234 may be one or more sensors used to determine a degree of contact apart from the detection of the biological signals used to provide the biosignal-based service.

When the additional sensor 234 enters an operating state based on a position at which the band portion 210 of bracelet is attached to the user 205, the determiner 220 may determine that the sensor unit 230 is closely attached to the user 205. For example, the force sensor of the additional sensor 234 may detect an increasing pressure from the user 205 based on a change in the position of the band portion 210 moving from a wrist to a forearm, and the determiner 220 may recognize the operating state of the force sensor. Accordingly, the determiner 220 may determine that the sensor unit 230 is closely attached to the user 205.

The determining of whether the sensor unit 230 is closely attached to the user 205 by the determiner 220 will be further described with reference to FIGS. 3A and 3B.

Figure 3A:
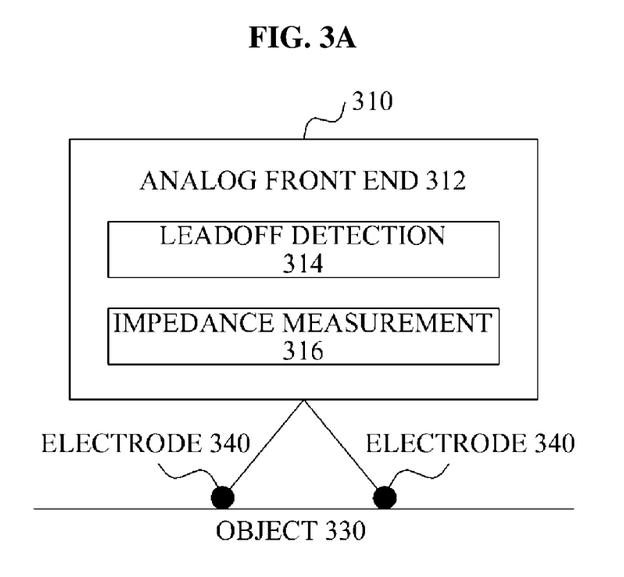
FIGS. 3A and 3B are diagrams illustrating examples of methods of determining whether a sensor is closely attached to a user.
Figure 3B:
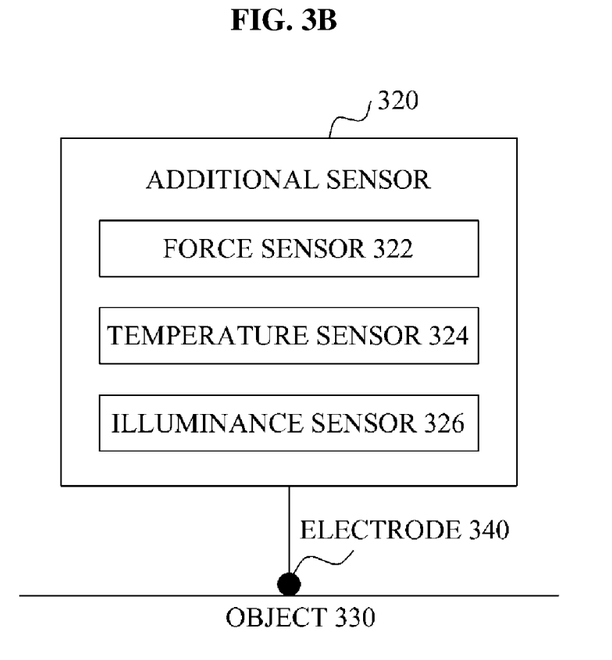

FIGS. 3A and 3B are diagrams illustrating examples of determining whether a bracelet is closely attached to an object.

Referring to FIG. 3A, an electrode 340 may be verified to be in a direct contact with the user 330 through leadoff detection 314 in an analog front end 312 of a sensor 310 or impedance measurement 316.

The electrode 340 may be used along with another electrode 340 that may obtain a biosignal from the object 330. Also, the electrode 340 may be used for the leadoff detection 314 or the impedance measurement 316 by obtaining a signal or a microcurrent form the user 330.

The electrode 340 may operate by classifying a point in time at which the leadoff detection 312 or the impedance measurement 316 is performed and a point in time at which a biosignal is obtained. The electrode 340 may be used to determine whether the bracelet is in contact with the user 330 by performing the leadoff detection 312 or the impedance measurement 316 using a relatively small amount of power prior to provision of the biosignal-based service. Also, the electrode 340 may be used to obtain the biosignal from the user 330 using a relatively greater amount of power after the bracelet is determined to be in contact with the user 330.

In an example of performing the leadoff detection 314, an analog front end 312 may send a signal to the user 330 through a front electrode of the electrode 340. In the event that the signal returns to a rear electrode of the electrode 340 via the user 330, the electrode 340 may be estimated to be in a lead-on state in which the electrode 340 is in a direct contact with the user 330. In response to the electrode 340 being estimated to be in a lead-on state, the determiner 220 may determine that the bracelet is closely attached to the user 330 and allow the electrode 340 to obtain the biosignal; thus, a wearable mobile device may establish a condition under which a biosignal-based service may be provided.

Conversely, in the event that the signal sent from the front electrode of the electrode 340 does not return to the rear electrode of the electrode 340 after a predetermined period of time elapses, the electrode 340 may be estimated to be in a lead-off state in which the electrode 340 is not in contact with the user 330. The determiner 220 may determine that the bracelet is not closely attached to the user 330 and may allow a service unrelated to the biosignal to be provided to the user.

In another example of performing the leadoff detection 314, the determiner 220 may analyze a waveform of a biosignal obtained through the electrode 340 of the analog front end 312, and determine whether the electrode 340 is in an exact contact with the user 330 or separated from the user 330. For example, in the event that a curve of the waveform of the biosignal changes drastically at an arbitrary point in time, the determiner 220 may determine, at a software level, that the electrode 340 is in the lead-off state in which the electrode 340 is separated from the user 330.

Also, in an example of performing the impedance measurement 316, the analog front end 312 may send a microcurrent to the user 330 through the electrode 340 and receive a return of the microcurrent from the user 330. Subsequently, the determiner 220 may calculate an impedance with respect to the user 330 based on the returned microcurrent, and may compare the calculated impedance to a predetermined value. In the event that the calculated impedance exceeds the predetermined value as a result of the comparison, the determiner 220 may determine that the sensor 310 is closely attached to the user 330 and may allow the electrode 340 to obtain the biosignal; thus, the wearable mobile device may prepare an environment in which the biosignal-based service is provided.

Conversely, in response to a determination that the calculated impedance does not satisfy the predetermined value as a result of the comparison, the determiner 220 may determine that the bracelet is not closely attached to the user 330 and may allow a service unrelated to the biosignal to be provided.

FIG. 3B is a diagram illustrating an example of a method of determining whether a bracelet is closely attached to the user 330 by an additional sensor 320.

Referring to FIG. 3B, the additional sensor 320 may be additionally included in the bracelet for detecting whether a biosignal detection sensor is closely attached to the user 330. The additional sensor 320 may include a force sensor 322, a temperature sensor 324, and an illuminance sensor 326.

The force sensor 322 may detect changes in pressure from the user 33 based on a position at which the bracelet is attached to the user 330 and may estimate whether the bracelet is closely attached to the user 330. For example, in the event that the force sensor 322 detects an increase in pressure "SW_ON" and an operating state of the force sensor 322 is recognized, the determiner 220 may estimate that the position at which the bracelet is attached to the user 330 changes from a wrist to a forearm and determine that the bracelet is closely attached to the user 330. Conversely, in the event that the force sensor 322 detects a decrease in pressure "SW_OFF" and the operating state of the force sensor 322 is not recognized, the determiner 220 may estimate that the position at which the bracelet is attached to the user 330 changes from the forearm to the wrist and determine that the bracelet is loosely attached to the user 330.

The temperature sensor 324 may detect changes in temperature emitted from the user 330 based on the position at which the bracelet is attached to the user 330 and estimate whether the bracelet is closely attached to the user 330. For example, when the temperature sensor 324 detects an increase in temperature "SW_ON" to be greater than or equal to a threshold temperature, for example, 31° C. indicating a temperature of skin, and an operating state of the temperature sensor 324 is recognized, the determiner 220 may estimate that the position at which the bracelet is attached to the user 330 moves towards the forearm having a relatively greater circumference and determine that the bracelet is closely attached to the user 330. Conversely, when the temperature sensor 324 detects a decrease in temperature "SW_OFF" to be less than the threshold temperature and the operating state of the temperature sensor 324 is not recognized, the determiner 220 may estimate that the position at which the bracelet is attached to the user 330 moves towards the wrist having a relatively smaller circumference and determine that the bracelet is loosely attached to the user 330.

Similarly, the illuminance sensor 326 may detect changes in brightness in the user 330 based on a degree of contact between the bracelet and the user 330 and estimate whether the bracelet is closely attached to the user 330. For example, when the illuminance sensor 326 detects a decrease in brightness "SW_ON" to be less than a threshold illuminance, for example, 10 lux (lx) indicating an illuminance of skin, and an operating state of the illuminance sensor 326 is recognized, the determiner 220 may estimate that the position at which the bracelet is attached to the user 330 moves towards the forearm from the wrist and determine that the bracelet is closely attached to the user 330. Conversely, when the illuminance sensor 326 detects an increase in illuminance "SW_OFF" to be greater than or equal to the threshold illuminance and the operating state of the illuminance sensor 326 is not recognized, the determiner 220 may estimate that the position at which the bracelet is attached to the user 330 moves towards the wrist from the forearm and determine that the bracelet is loosely attached to the user 330.

Thus, the determiner 220 may determine whether the bracelet is closely attached to the user 330 in conjunction with the operating state of the additional sensor 320.

Referring back to FIG. 2, when the sensor unit 230 includes the sensor 232 and is determined to be closely attached to the user 205, the sensor unit 230 may be activated and detect a biosignal from the user 205. The sensor unit 230 may be in contact with the user 205 and monitor a biosignal generated by the user 205.

The user 205 may indicate a muscle of an organism from which a biosignal is required to be measured, for example, a wrist muscle and a forearm muscle.

The sensor unit 230 may include the sensor 232, for example, an ECG sensor, a PPG sensor, an impedance sensor, an EMG sensor, an iris recognition sensor, and a fingerprint recognition sensor, that may collect signals from the user 205. Thus, the sensor unit 230 may detect various biosignals generated from the muscle using the sensor 232.

The biosignals may include, for example, a bioelectric/biomagnetic signal, a bioimpedance signal, a biomechanical signal, and the like that may be generated from the muscle.

Also, the sensor unit 230 may detect a gesture performed in association with the user 205 based on a pattern of a detected biosignal. For example, the sensor unit 230 may distinguish a difference in the pattern of the detected biosignal and differently recognize a gesture of clenching a first and a gesture of folding a finger.

To detect the biosignals, the sensor unit 230 may identify an activated sensor of the sensor 232 based on a position at which the wearable mobile device 200 is closely attached to the user 205 and detect the biosignals using the identified sensor. For example, when the wearable mobile device 200 is determined to be closely attached to an upper arm, the sensor unit 230 may activate a biometric sensor of the sensor 232 and perform an individual user authentication. Also, when the wearable mobile device 200 is determined to be closely attached to a lower arm, the sensor unit 230 may activate an EMG sensor of the sensor 232 and obtain an EMG signal to recognize a gesture of the user. Similarly, when the wearable mobile device 200 is determined to be closely attached to a wrist, the sensor unit 230 may activate a PPG sensor and measure heart rates of the user.

The wearable mobile device 200 may selectively provide a biosignal-based service by determining whether the wearable mobile device 200 is closely attached to the user 205.

To perform the foregoing, the wearable mobile device 200 may further include the controller 240.

When the wearable mobile device 200 is determined to be closely attached to the user 205, the controller 240 may execute a program associated with the biosignals or adjust a system environment to be a predetermined value. The controller 240 may automatically execute a program for detecting the biosignals from the user 205 or a predetermined program using the detected biosignals.

For example, when the wearable mobile device 200 is determined to be closely attached to the user 205, the controller 240 may automatically change a configuration of the wearable mobile device 200 to which the biosignal-based service is provided.

Also, when the wearable mobile device 200 is closely attached to the user 205, the controller 240 may automatically execute an application for analyzing the biosignals detected through the activated sensor unit 230 or automatically terminate an application without having a direct connection to the biosignals.

When the wearable mobile device 200 is not closely attached to the user 205, the controller 240 may control the executed program to be suspended or restore the adjusted system environment to be an original value. Also, when the wearable mobile device 200 is not closely attached to the user 205, the controller 240 may control the sensor unit 230 to be inactivated and to suspend the detection of the biosignals.

The wearable mobile device 200 may further include the output unit 250 that may output a result of the determining of whether the wearable mobile device 200 is closely attached to the user 205.

When the wearable mobile device 200 is closely attached to the user 205, the output unit 250 may provide, as the biosignal-based service, the result output by the program associated with the biosignals and automatically executed.

When the wearable mobile device 200 is closely attached to the user 205, the output unit 250 may provide a result of detecting the biosignals and information about the execution of the program.

For example, when the wearable mobile device 200 is closely attached to the user 205, the output unit 250 may output, as the biosignal-based service, an exercise management service associated with heart rates measured by the PPG sensor.

For another example, the output unit 250 may output, as the biosignal-based service, a gesture control service for a home appliance using the biosignals based on a movement of the user 205.

For still another example, the output unit 250 may output, as the biosignal-based service, an individual authentication service associated with the impedance measured by the EMG sensor.

Also, when the wearable mobile device 200 is closely attached to the user 205, the output unit 250 may output feedback indicating an ability to detect a biosignal through one of vision, vibration, and sound. Conversely, when the wearable mobile device 200 is not closely attached to the user 205, the output unit 250 may output feedback indicating an inability to detect a biosignal through one of vision, vibration, and sound.

The wearable mobile device 200 may automatically provide a suitable service associated with a biosignal by allowing the user to simply determine whether the band portion 210 of the bracelet is to be loosely or tightly attached to the forearm. Accordingly, the wearable mobile device 200 may provide a high level of convenience to the user.

When the user loosely attaches the band portion 210 of the bracelet, the wearable mobile device 200 may automatically cease detection of a biosignal using the sensor unit 230. Accordingly, the wearable mobile device 200 may adequately control use of a large amount of power that may be consumed due to a conventional method of permanently detecting a biosignal.

An operation of the wearable mobile device 200 will be further described hereinafter.

Figure 4:
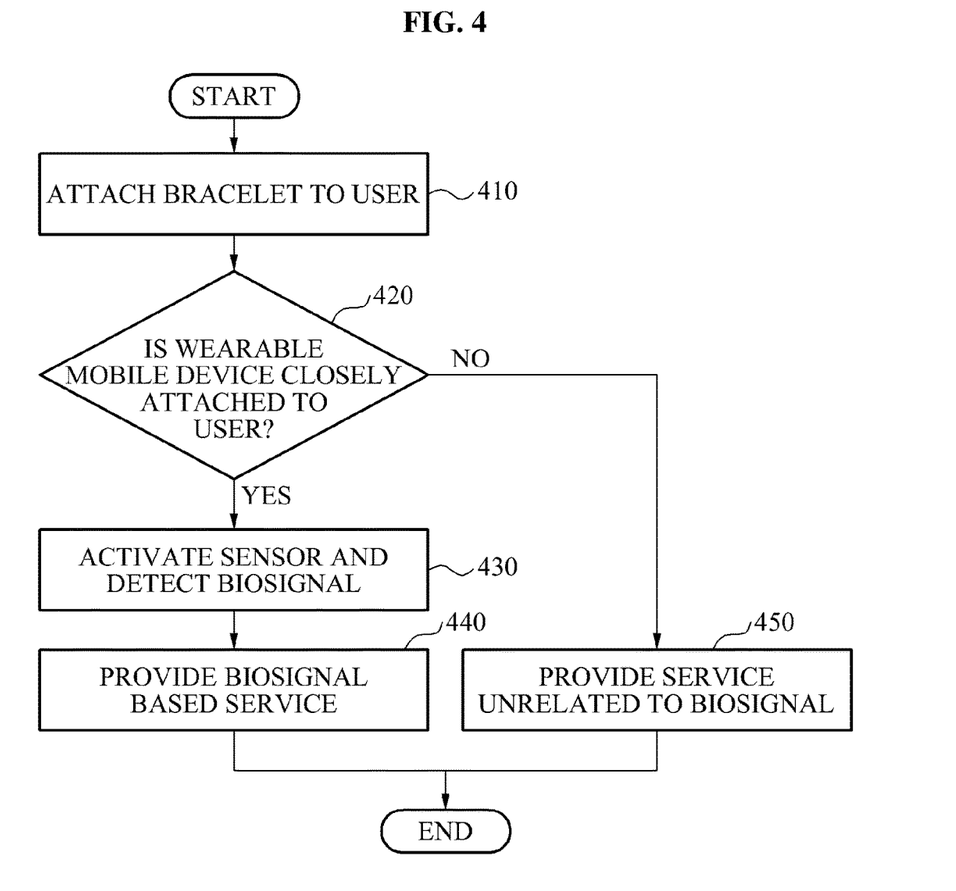
FIG. 4 is a flowchart illustrating an example of a method of a wearable mobile device selectively using biosignals.

FIG. 4 is a flowchart illustrating an example of a method of using the wearable mobile device 200 of FIG. 2 to selectively detect a biosignal.

In 410, the band portion 210 of the wearable mobile device 200 is attached to the user 205 by surrounding a body part of the user 205. Operation 410 may allow the wearable mobile device 200 to be worn by the user 205, a target to be measured, using the bracelet 210.

The bracelet 210 may include the at least one sensor 232 that may be disposed at regular intervals in the sensor unit 230. When the bracelet 210 is being attached to the user 205, the sensor 232 in the sensor unit 230 may be fixed to allow a sensing surface to be in contact with the user 205. The sensing surface may refer to a surface on which the sensor 232 that may directly detect a biosignal generated from the user 205 while being in direct contact with the user 205 are disposed. For example, the wearable mobile device 200 may detect a wide range of biosignals, for example, a bioelectric/biomagnetic signal, a bioimpedance signal, and a biodynamical signal, in association with the user 205 through the sensor unit 230.

The band portion 210 may be initially attached to a wrist of a user, and move towards a forearm of the user to acquire a biosignal-based service based on an intention of the user, so that the sensing surface on which the sensor unit 230 is disposed may be closely attached to skin of the forearm. When the wearable mobile device 200 is determined to be closely attached to the body of the user 205, the sensor unit 230 may collect biosignals through the sensor 232 of the sensing unit 230 from all ranges of a forearm muscle, which may be the body part of the user 205 to which the wearable mobile device 200 is attached.

In 420, the wearable mobile device 200 may determine whether the wearable mobile device 200 is closely attached to the user 205 based on a movement of the wearable mobile device 200 during attachment of the wearable mobile device 200 to the user 205. Operation 420 may be a process of preparing an environment in which the biosignal-based service is selectively provided after a degree of contact between the sensor unit 250 on the band portion 210 and the user 205 is verified.

In 420, the wearable mobile device 200 may measure a range or a position at which the band portion 210 of the bracelet is in contact with the user 205, and may determine that the sensor unit 250 of the band portion 210 is closely attached to the user 205 in response to the measured range satisfying a predetermined standard value or the measured position corresponding to a predetermined skin area in the user 205.

In an example, the wearable mobile device 200 may determine whether the band portion 210 of the bracelet is closely attached to the user 205 through an analog front end of the sensor 232 that may be in contact with the user 205. The analog front end may indicate a front electrode and a rear electrode of the sensor 232 that may be responsible for detection.

When the analog front end is not in a leadoff state, the wearable mobile device 200 may determine that the band portion 210 is closely attached to the user 205. The wearable mobile device 200 may determine that the wearable mobile device 200 is closely attached to the user 205 by verifying the leadoff state in which the wearable mobile device 200 is slightly separated from the user 205 and the analog front end is not able to optimally collect signals. For example, the analog front end may send a signal to the user 205 at a point in time when the wearable mobile device 200 is attached to the user 205. When the analog front end receives a return of the signal from the user 205, the wearable mobile device 200 may determine that the analog front end is in an actual contact with the user 205 and not in the leadoff state. Simultaneously, the wearable mobile device 200 may determine that the wearable mobile device 200 is closely attached to the user 205.

In another example, the wearable mobile device 200 may determine whether wearable mobile device 200 is closely attached to the user 205 using a microcurrent sent from the analog front end to the user 205. When an impedance measured based on the return of the sent microcurrent satisfies a predetermined value, the wearable mobile device 200 may determined that the wearable mobile device 200 is closely attached to the user 205. For example, in response to the microcurrent sent from the analog front end to the user 205 at a point in time when the analog front end is placed into contact with the user 205, the wearable mobile device 200 may calculate the impedance based on the microcurrent returned from the user 205, and determine that the wearable mobile device 200 is closely attached to the user 205 by identifying that the calculated impedance exceeds the predetermined standard value, for example, 100 mΩ.

In still another example, the wearable mobile device 200 may determine that wearable mobile device 200 is closely attached to the user 205 using the additional sensor 234 that may be additionally included in the band portion 210 of the wearable mobile device 200. The additional sensor 234 may include a temperature sensor used to detect a temperature emitted from the user 205, a force sensor used to detect pressure applied by the user 205, an illuminance sensor used to detect brightness in the user 205 based on a degree of contact, and the like.

When the additional sensor 234 enters an operating state, the wearable mobile device 200 may determine that wearable mobile device 200 is closely attached to the user 205, based on a position at which the wearable mobile device 200 is attached to the user 205. For example, when the position of the wearable mobile device 200 moves from the wrist to the forearm, the force sensor of the additional sensor 234 may detect an increase in pressure from the user 205, and the wearable mobile device 200 determine that the wearable mobile device 200 is closely attached to the user 205 by recognizing the operating state of the force sensor.

In 430, when the wearable mobile device 200 is determined to be closely attached to the user in operation 420 (in a YES direction), the wearable mobile device 200 activates the sensor 232 in the sensor unit 230 and detects a biosignal from the user 205. Operation 430 may be a process of monitoring a biosignal generated from the user 205 during attachment of the wearable mobile device 200 to the user 205.

The user 205 may indicate a muscle of an organism from which a biosignal is required to be detected, for example, a wrist muscle and a forearm muscle.

The sensor unit 230 may include the sensor 232 such as an ECG sensor, a PPG sensor, an impedance sensor, an EMG sensor, an iris recognition sensor, and a fingerprint recognition sensor, and the like, and detect various biosignals generated from the muscle using the sensor 232.

The biosignals may include a bioelectric/biomagnetic signal, a bioimpedance signal, a biomechanical signals, and the like, generated from the muscle.

Also, the wearable mobile device 200 may detect a gesture associated with the user 205 based on a pattern of a detected biosignal through the sensor unit 230. For example, the wearable mobile device 200 may distinguish a difference in the pattern of the detected biosignal, and differently detect a gesture of clenching a first by the user or a gesture of folding a finger.

To detect a biosignal, the wearable mobile device 200 may identify an activated sensor among the sensor 232 based on a position at which the wearable mobile device 200 is closely attached to the user 205, and detect the biosignal using the identified sensor. For example, when the wearable mobile device 200 is determined to be closely attached to an upper arm, the wearable mobile device 200 may activate a biometric sensor of the sensor 232 and perform an individual user authentication. Also, when the wearable mobile device 200 is determined to be closely attached to a lower arm, the wearable mobile device 200 may activate an EMG sensor of the sensor 232 and obtain an EMG signal to recognize a gesture by the user. Similarly, when the wearable mobile device 200 is determined to be closely attached to a wrist, the wearable mobile device 200 may activate a PPG sensor of the sensor 232 and measure heart rates of the user.

In 440, the wearable mobile device 200 provides a selective biosignal-based service when the wearable mobile device 200 is determined to be closely attached to the user 205.

In 440, the wearable mobile device 200 executes a program associated with the biosignal or adjusts a system environment to be a predetermined value. The wearable mobile device 200 may automatically execute a program for detecting a biosignal from the user 205 or a predetermined program using the detected biosignal.

For example, when the wearable mobile device 200 is determined to be closely attached to the user 205, the wearable mobile device 200 may automatically change a configuration of the wearable mobile device 200 to be a configuration in which the biosignal-based service is provided.

Also, when the wearable mobile device 200 is determined to be closely attached to the user 205, the wearable mobile device 200 may automatically execute an application for analyzing the biosignal detected through the activated sensor of the sensor 232 in the sensor unit 230 or automatically terminate an application that may not be directly related to the biosignal.

Further, the wearable mobile device 200 may output a result of the determining of whether the wearable mobile device 200 is closely attached to the user 205. The wearable mobile device 200 may provide, as the biosignal-based service, a result output by the program associated with the biosignal that may be automatically executed based on the result of the determining.

For example, the wearable mobile device 200 may output, as the biosignal-based service, an exercise management service associated with heart rates measured by the PPG sensor based on the result of the determining.

For another example, the wearable mobile device 200 may output, as the biosignal-based service, a gesture control service for a home appliance using a biosignal based on a movement of the user 205.

For still another example, the wearable mobile device 200 may output, as the biosignal-based service, an individual authentication service associated with an impedance to be measured by the EMG sensor.

Also, when the wearable mobile device 200 is closely attached to the user 205, the wearable mobile device 200 may output feedback indicating an ability to measure a biosignal through one of vision, vibration, and sound. Conversely, when the wearable mobile device 200 is not closely attached to the user 205, the output unit 250 of the wearable mobile device 200 may output feedback indicating an inability to measure the biosignal through one of vision, vibration, and sound.

In 450, when the wearable mobile device 200 is determined not to be closely attached to the user 205 in operation 420 (in a NO direction), the wearable mobile device 200 may provide a service unrelated to a biosignal. Operation 450 may be a process of providing a communication service with a connected terminal or a service that may not be directly related to the biosignal.

For example, when the wearable mobile device 200 is not closely attached to the user 205, the wearable mobile device 200 may provide visual information about a quantity of terminal utilization that may be verified by an accelerometer.

Also, when the wearable mobile device 200 is not closely attached to the user 205, the wearable mobile device 200 may control the executed program to stop or restore the adjusted system environment to be an original value, as the biosignal-based service in operation 440.

When the wearable mobile device 200 is not closely attached to the user 205, the wearable mobile device 200 may control the sensor 232 in the sensor unit 230 to be in an inactivated state and to cease detection of a biosignal.

The wearable mobile device 200 may automatically provide, to a user, a suitable service associated with a biosignal of the user by allowing the user to simply determine whether the wearable mobile device 200 is to be loosely attached to a wrist or tightly attached to a forearm and thus, a high level of convenience may be provided to the user.

When the user loosely attaches the wearable mobile device 200, the wearable mobile device 200 may automatically stop allowing the sensor unit 230 to measure a biosignal. Thus, the wearable mobile device 200 may adequately control use of a vast amount of power consumed for permanent measurement of biosignals in conventional usage.

The units described herein may be implemented using hardware components and software components. For example, the hardware components may include microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device. Examples of the non-transitory computer readable recording medium include read-only memory (ROM), random-access memory (RAM), CD-ROMs, magnetic tapes, floppy disks, optical data storage devices. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

As a non-exhaustive illustration only, a terminal or device described herein may refer to mobile devices such as a cellular phone, a personal digital assistant (PDA), a digital camera, a portable game console, and an MP3 player, a portable/personal multimedia player (PMP), a handheld e-book, a portable laptop PC, a global positioning system (GPS) navigation, a tablet, a sensor, and devices such as a desktop PC, a high definition television (HDTV), an optical disc player, a setup box, a home appliance, and the like that are capable of wireless communication or network communication consistent with that which is disclosed herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of measuring a biosignal, the method comprising:
   measuring a proximity, a body information, or a biometric information comprising any one or any two or more of a skin, blood flow, and heart rate;
   determining whether an attached wearable mobile device is closely attached to a user or loosely attached to the user based on the measured proximity, body information, or biometric information;
   providing a first service in response to the wearable mobile device being determined to be closely attached to the user and providing a second service to the user in response to the wearable mobile device being determined to be loosely attached to the user,
   measuring a range or a position at which the wearable mobile device contacts the user;
   determining that the wearable mobile device is closely attached to the user in response to the measured range satisfying a standard value or in response to the measured position corresponding to a skin area of the user; and
   determining that the wearable mobile device is loosely attached to the user when the wearable mobile device is located at a wrist area of the user,
   wherein the standard value and the skin area of the user correspond to the wearable mobile device being positioned at a skin area of the user that has a greater circumference than a wrist area of the user.

2. The method of claim 1, further comprising:
   providing a biosignal-based service in response to the wearable mobile device being determined to be measuring a range or a position at which the wearable mobile device contacts the user.

3. The method of claim 1, wherein the providing of the first service further comprises:
   executing a program for measuring a biosignal from the user or a program that uses a measured biosignal; and
   providing a result from the executed program as the first service.

4. A wearable mobile device method, the method comprising:
   measuring a proximity, a body information, or a biometric information comprising any one or any two or more of a skin, blood flow, and heart rate;
   determining whether a bracelet, as a wearable mobile device, is closely attached to a user or loosely attached to the user based on the proximity, the body information, or the biometric information;
   sensing a biosignal from the user by activating a sensor, configured to sense the biosignal from the user, of the bracelet in response to the bracelet being determined to be closely attached to the user;
   measuring a range or a position at which the bracelet contacts the user;
   determining that the bracelet is closely attached to the user in response to the measured range satisfying a standard value or in response to the measured position corresponding to a skin area of the user; and
   determining that the bracelet is loosely attached to the user when the bracelet is located at a wrist area of the user,
   wherein the standard value and the skin area of the user correspond to the wearable mobile device being positioned at a skin area of the user that has a greater circumference than a wrist area of the user.

5. The method of claim 4, further comprising:
   determining that the bracelet is closely attached to the user in response to an analog front end of the sensor being in a lead-on state and determining that the bracelet is loosely attached to the user in response to the analog front end of the sensor being in a lead-off state, the analog front end of the sensor being arranged in the bracelet so that the lead-on state indicates that the sensor is in contact with a body portion of the user sufficient to sense the biosignal and the lead-off state indicates that that the sensor is not in contact with the body portion sufficient to sense the biosignal.

6. The method of claim 4, further comprising:
   sending a microcurrent to the user through an analog front end of the sensor; and
   determining that the bracelet is closely attached to the user in response to an impedance measured based on a return of the sent microcurrent satisfying the standard value and determining that the bracelet is loosely attached to the user in response to the measured impedance not satisfying the standard value.

7. The method of claim 4, further comprising:
   determining that the bracelet is closely attached to the user in response to an additional sensor of the bracelet, for determining whether the bracelet is closely attached or loosely attached to the user, entering an operating state based on a body position at which the bracelet is attached to the user.

8. The method of claim 4, further comprising:
   identifying which sensors of the bracelet to activate to sense respective biosignals based on a positioning of the bracelet while the bracelet is attached to the user; and
   sensing the respective biosignals.

9. The method of claim 4, further comprising:
   in response to determining that the bracelet is closely attached to the user, executing a program associated with the biosignal or adjusting a system environment to be a predetermined value; and
   in response to determining that the bracelet is loosely attached to the user, deactivating the sensor.

10. The method of claim 4, further comprising:
    outputting a result of the determining of whether the bracelet is closely or loosely attached to the user.

11. The method of claim 4, further comprising;
providing a first service to the user in response to the bracelet being determined to be closely attached to the user and providing only second services to the user in response to the bracelet being determined to be loosely attached to the user.

12. The method of claim 10, further comprising;
deactivating the sensor in response to the bracelet being determined to be loosely attached to the user.

13. A wearable mobile device, comprising:
a bracelet, as the wearable mobile device, configured to be attached to a user by at least partially surrounding a body portion of the user;
a determiner configured to measure a proximity, a body information, or a biometric information comprising any one or any two or more of a skin, blood flow, and heart rate, and to determine whether the bracelet is closely attached to the user or loosely attached to the user based on the proximity, the body information, or the biometric information; and
a sensor unit comprising a sensor configured to sense a biosignal from the user subsequent to activation of the sensor in response to the determiner determining that the bracelet is closely attached to the user,
wherein the sensor unit measures a range or a position at which the wearable mobile device contacts the user,
wherein the determiner determines that the wearable mobile device is closely attached to the user in response to the measured range satisfying a standard value or in respond to the measured position corresponding to a skin area of the user, and determines that the wearable mobile device is loosely attached to the user when the wearable mobile device is located at a wrist area of the user, and
wherein the standard value and the skin area of the user correspond to the wearable mobile device being positioned at a skin area of the user that has a greater circumference than a wrist area of the user.

* * * * *